United States Patent [19]

Faasse, Jr.

[11] Patent Number: 5,566,672
[45] Date of Patent: Oct. 22, 1996

[54] BIOMEDICAL ELECTRODE

[75] Inventor: Adrian L. Faasse, Jr., Caledonia, Mich.

[73] Assignee: Labeltape Meditect, Inc.

[21] Appl. No.: 241,665

[22] Filed: May 12, 1994

Related U.S. Application Data

[63] Continuation-in-part of Ser. No. 176,777, Jan. 3, 1994, abandoned.

[51] Int. Cl.[6] .......................... A61B 5/0408; A61N 1/04
[52] U.S. Cl. ...................... 128/640; 128/641; 607/149; 607/152
[58] Field of Search ................................. 128/639–641, 128/644; 607/149, 152, 153

[56] References Cited

U.S. PATENT DOCUMENTS

| | | |
|---|---|---|
| Re. 31,454 | 12/1983 | Hymes . |
| D. 238,971 | 2/1976 | Nardi et al. . |
| D. 240,166 | 6/1976 | Cartmell et al. . |
| D. 297,460 | 8/1988 | Inoue et al. . |
| 2,047,308 | 7/1936 | Chapman . |
| 3,389,703 | 6/1968 | Criswell et al. . |
| 3,746,004 | 7/1973 | Jankelson . |
| 3,817,252 | 6/1974 | Maurer . |
| 3,817,253 | 6/1974 | Gonser . |
| 3,848,600 | 11/1974 | Patrick, Jr. et al. . |
| 4,126,126 | 11/1978 | Bare et al. . |
| 4,155,354 | 5/1979 | Rasmussen . |
| 4,166,465 | 9/1979 | Esty et al. . |
| 4,274,420 | 6/1981 | Hymes . |
| 4,308,870 | 1/1982 | Arkans . |
| 4,332,257 | 6/1982 | Ayer . |
| 4,384,582 | 5/1983 | Watt . |
| 4,387,714 | 6/1983 | Geddes et al. . |
| 4,393,584 | 7/1983 | Bare et al. . |
| 4,422,461 | 12/1983 | Glumac . |
| 4,522,211 | 6/1985 | Bare et al. . |
| 4,539,996 | 9/1985 | Engel . |
| 4,559,950 | 12/1985 | Vaughan et al. . |
| 4,583,547 | 4/1986 | Granek et al. . |
| 4,617,935 | 10/1986 | Cartmell et al. . |
| 4,633,879 | 1/1987 | Ong . |
| 4,674,512 | 6/1987 | Rolf . |
| 4,679,563 | 7/1987 | Wada et al. . |
| 4,679,564 | 7/1987 | Sessions . |
| 4,694,835 | 9/1987 | Strand . |
| 4,700,710 | 10/1987 | Hoffman . |
| 4,706,680 | 11/1987 | Keusch et al. ........................ 128/640 |
| 4,722,761 | 2/1988 | Cartmell et al. . |
| 4,768,514 | 9/1988 | De Marzo . |
| 4,809,699 | 3/1989 | Shimizu et al. ........................ 128/640 |
| 5,012,810 | 5/1991 | Strand et al. . |
| 5,078,139 | 1/1992 | Strand et al. . |
| 5,133,355 | 7/1992 | Strand et al. . |
| 5,133,356 | 7/1992 | Bryan et al. . |
| 5,215,087 | 6/1993 | Anderson et al. ...................... 128/640 |
| 5,217,014 | 6/1993 | Hahn et al. . |

FOREIGN PATENT DOCUMENTS

| | | |
|---|---|---|
| 0040658 | 12/1981 | European Pat. Off. . |
| 275628 | 7/1988 | European Pat. Off. ............... 128/640 |
| 9105509 | 5/1991 | WIPO .................................. 128/640 |

*Primary Examiner*—Lee S. Cohen
*Attorney, Agent, or Firm*—Price, Heneveld, Cooper, DeWitt & Litton

[57] ABSTRACT

A tab electrode includes a flexible insulative layer having a first and second opposite side terminating in a peripheral edge and having a tab defined therein inboard of the peripheral edge. A conductive member, having a first end and a second end is adhered to the first side of the insulative layer with the second end underlying the tab. A conductive gel is attached to the first end of the conductive member on a side opposite that of the flexible insulative layer. A lower insulative layer is adhered to the first side of the flexible insulative layer exposing the conductive gel and underlying the second end of the conductive member. The electrode construction is such that the second end of the conductive member extends above and away from the body of the electrode when the electrode is flexed or adhered to a curved surface such as the chest cavity of the patient. In this manner, the electrode lead can be easily and quickly fastened to the tab.

37 Claims, 4 Drawing Sheets

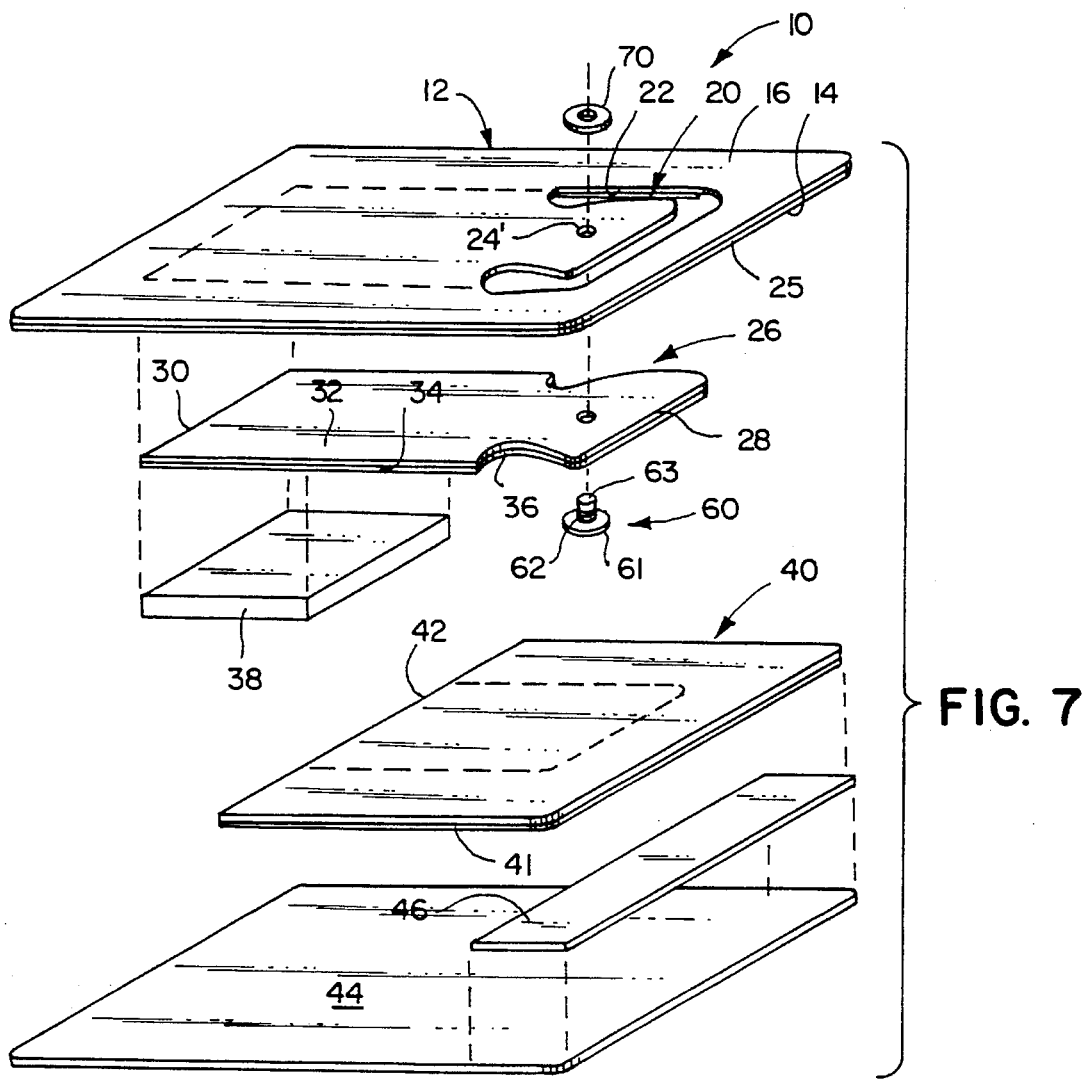
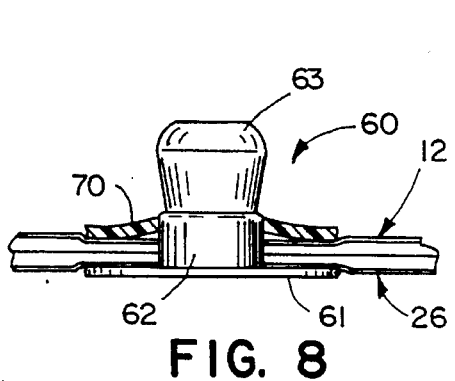
FIG. 8
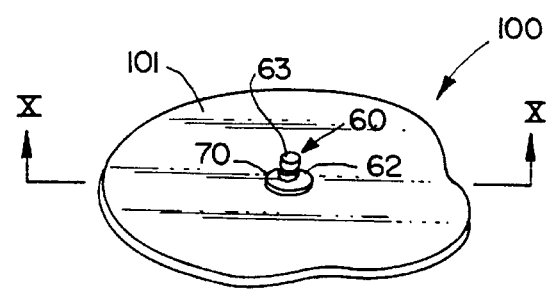
FIG. 9

BIOMEDICAL ELECTRODE

This application is a continuation-in-part of application Serial No. 08/176,777, filed Jan. 3, 1994, now abandoned, and entitled "BIOMEDICAL ELECTRODE."

FIELD OF THE INVENTION

The present invention relates to disposable, biomedical electrodes through which an electrical current enters or is detected in a patient's body, and particularly to a biomedical electrode having an off-set tab providing improved electrical contact with the patient's body, resulting in fewer transient signals caused by interruption of the contact or shorting against the patient's body. The present invention is useful for monitoring/diagnosing a patient's physiological condition and may be adapted for use as a transcutaneous electrical nerve stimulation (TENS) electrode.

BACKGROUND OF THE INVENTION

The principal functional components of a typical electrode include a conductive layer, a conductive contact to which leads from a monitoring/diagnostic or TENS apparatus can be connected, and a support member upon which the two aforementioned components are mounted. Generally, the support member or carrier has an adhesive backing so that the electrode can be securely fastened to the patient. The conductive layer is typically a conductive hydrogel while the conductive contact may consist of either a metallic snap-fastener or a conductive tab.

In U.S. Pat. No. 3,977,392, the conductive hydrogel and the metallic snap-fastener are spaced apart from each other on the carrier medium. A strip of conductive material, such as silver foil, acts as a bridge between the two components to complete the electrical connection. Such a configuration is known as an off-set electrode. Off-set snap-fastener electrodes are known to have advantages over electrodes which intimately contact the snap fastener to the hydrogel, since in the latter configuration corrosion of the snap fastener is increased. This corrosion jeopardizes the accuracy of the electrode, making it all but useless. A drawback to off-set snap electrodes is that the snap must be fastened to the electrode carrier medium, resulting in a relatively slow and expensive construction. It requires one to start and stop the manufacturing process so a stud may be inserted through the material and then moved on to another location where the snap is then pressed onto the stud and planted in place. Accordingly, snap electrodes are expensive.

Tab electrodes include a conductive hydrogel in contact with a metal film or foil having a tab defined at the peripheral edge of the electrode to receive a clip. In early electrodes, the tab typically projected from the peripheral edge of the electrode. A disadvantage with this electrode construction is that the application of a tensional load on the tab often resulted in the peeling of the electrode from the patient's body, or the pulling of the pad portion of the conductive member away from the patient's body, resulting in a break in electrical contact.

U.S. Pat. No. 4,674,512 teaches a rectangular electrode which has been die-cut with a U-shaped cut in the center portion to provide a U-shaped tab at the center. The lower surface of the tab and a portion of the electrode include a conductive layer which comprises a metal or metal alloy. The conductive layer, with the exception of the tab, is uniformly underlain by a conductive flexible substrate or matrix to contact the skin. The conductive layer and the matrix are positioned concentrically within a larger area of the electrode such that the lower portion of the electrode extends beyond the edge of the conductive layer to provide a peripherally extending, downwardly facing exposed pressure-sensitive surface to adhere to the skin. A disadvantage with this construction is that the conductive tab overlies the patient's skin, making it possible for the clip to make direct contact with the patient's skin to introduce a transient signal or gap ground contact.

U.S. Pat. No. 5,012,810 discloses an electrode having a conductive member oriented relative to the upper insulator construction so that the pad portion of the conductor member is positioned on the first side of the insulator construction, and the tab portion is positioned on the second, opposite side of the insulator construction. The insulator construction includes first and second sections, a substantially non-conductive material. Each section has an edge portion which includes a border portion. The electrode is oriented with the first and second sections, positioned substantially coplaner with one another, and with the edge portions opposed to and in overlapping relationship with one another. The conductor member is oriented in this arrangement with the tab portion projecting between the overlapping edge and border portions of the insulator construction. The tab still projects from a peripheral edge of one of the electrode sections. A further disadvantage with this construction is that a tensional force may pull the conductor member from between the two insulator sections, thus possibly causing transient or artifact signals. Furthermore, the construction of the '810 electrode is complicated in that it calls for two insulator sections which must be aligned and placed in overlapping relationship to seal one end of the conductive member from the opposite end receiving the electrode lead.

SUMMARY OF THE INVENTION

The present invention is an in-board tab electrode wherein a separate insulating layer underlies and is adhered to at least that portion of the electrode into which the tab projects. Insulating layer is not, however, adhered to the tab, and does not cover file skin engaging conductive material.

The present invention is of simple construction and provides a continuous conductive contact through an intermediary of electrically conductive gel or adhesive material which minimizes warm-up time and maintains the quality of the signal or trace. The electrode construction aids in avoiding motion artifacts, that is, disturbances in the trace due to relative movement between the electrode and the skin of the patient.

BRIEF DESCRIPTION OF THE DRAWING FIGURES

A better understanding of the invention and advantages provided thereby may be obtained by reference to the specification and the attached drawing figures, wherein:

FIG. 7 is an exploded perspective view of an alternative embodiment of the invention wherein a conductive connector post is secured to the tab of the electrode;

FIG. 8 is a cross-sectional view showing securement of the conductive connector post to the electrode;

FIG. 9 is a perspective view of an alternative embodiment electrode employing the conductive connector post.

DETAILED DESCRIPTION OF THE PREFERRED EMBODIMENT

Figure 1:
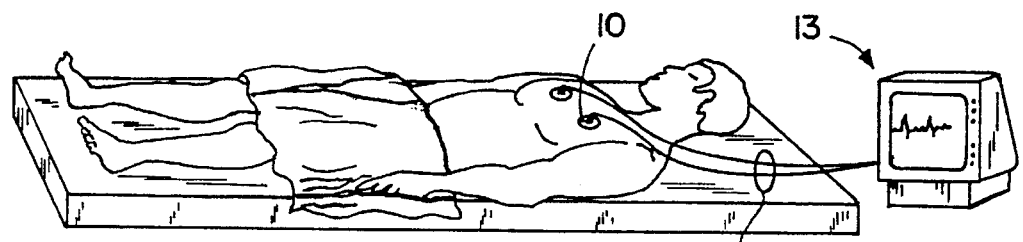
FIG. 1 illustrates the preferred embodiment electrode adhered to the chest of a patient.
Figure 2:
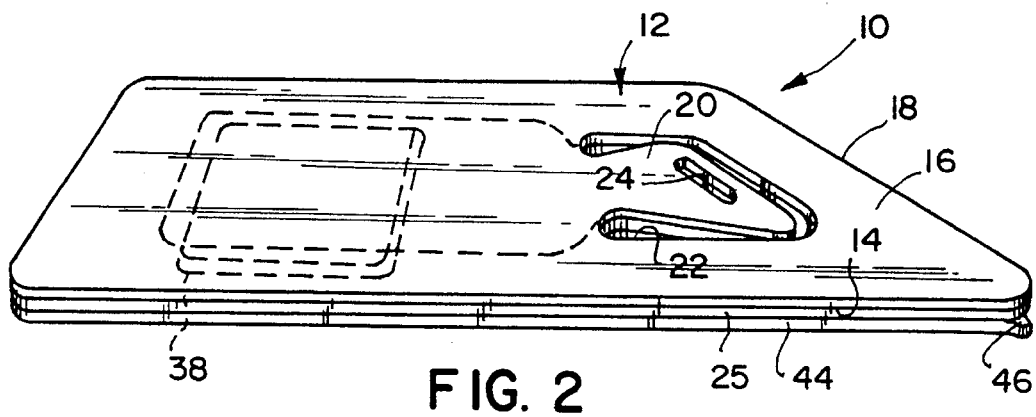
FIG. 2 is a perspective view of the electrode of the preferred embodiment.
Figure 3:
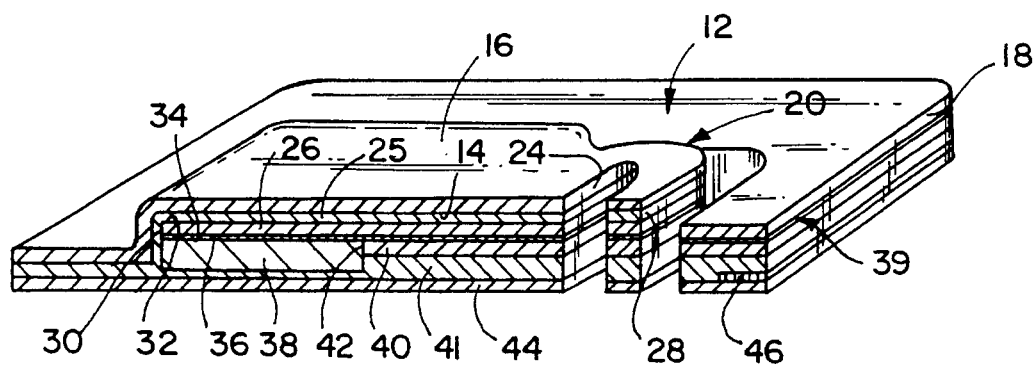
FIG. 3 is an elevational section view of the electrode taken along line II—II in FIG. 2.
Figure 4:
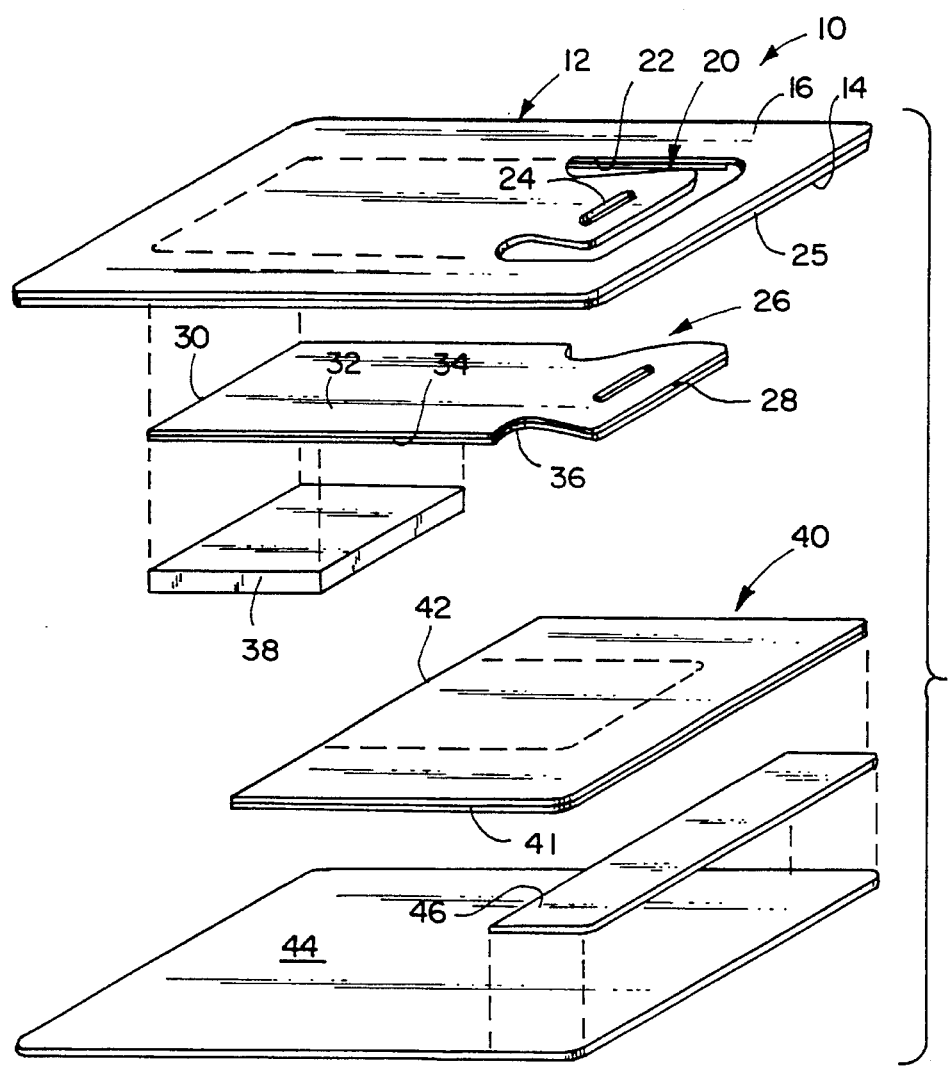
FIG. 4 is an exploded view of one embodiment of the electrode of the preferred embodiment.

Referring now to the drawing figures, a number of electrodes 10 are shown attached to the chest region of a patient and interconnected through a number of electrode leads 11 to a monitoring/diagnostic device 13 such as commonly used in monitoring a patient's heart. Although the invention is shown as a monitoring electrode, the same general principles illustrated by this invention may be applied to transcutaneous electrical nerve stimulation (TENS) electrodes used to stimulate a patient's muscles. Referring to FIGS. 2–4, preferred embodiment electrode 10 includes a top insulative layer 12 having a lower surface 14 and an opposite upper surface 16, terminating in a predetermined geometric shape such as a rectangle defined by peripheral edge 18. Insulative layer 12 is preferably made from a non-woven material such as a spun-bound polypropelyne, although other materials may also be used including plastic films such as vinyl, polyester, and the like, closed-cell foam such as polyethylene, and cloth and non-woven cloth materials. In the preferred embodiment, insulative layer 12 is die-cut from a sheet of the backing material in a generally rectangular shape approximately 5 centimeters (cm) by 3 cm. At the same time, a tab 20 is defined toward the center of one end, inboard from peripheral edge 18, by a U-shaped die-cut 22. A circular or oval hole 24 is also formed in tab 20. The lower surface 14 of insulative layer 12 preferably includes a skin adhesive layer 25 to adhere electrode 10 to the patient as well as act as a carrier for other component described below. Typically, acrylate ester adhesives such as acrylate ester copolymer adhesives generally described in U.S. Pat. No. 2,973,826 may be used. Although the preferred size of electrode 10 is as described above, the size and shape may vary depending upon the desired function.

Underlying insulative layer 12, and preferably disposed inboard from peripheral edge 18 along the longitudinal axis of layer 12, is a conductive member 26 having a first end 28 corresponding in shape to tab 20, and a second opposite end 30 spaced or off-set some distance from tab 20. Conductive member 26 includes a first side 32 oriented toward insulative layer lower surface 14, and on opposite surface 34 having a conductive coating or film 36. In the preferred embodiment, conductive member 26 is made from a polyester MYLAR™ film having a thickness within the range of 1 to 10 mils, and preferably within the range of 3 to 7 mils, and most preferably between 5 to 7 mils. At this thickness, the polyester MYLAR™ film is still flexible, but less flexible than top insulative layer 12 which assists in raising and exposing tab 20 when electrode 10 is flexed or adhered to a curved surface such as a patient's chest. The conductive coating or film 36 on lower surface 34 of conductive member 26 is preferably a flood-coat printed layer of silver/silver chloride. The thickness of the conductive coating or film 36 may be on the order 0.3 to 0.7 microns, and preferably 0.5 microns, but can vary so long as it is sufficient to carry an electrical current across the entire length of the conductive member 26. As an alternative to the printed conductive coating, conductive member 26 may also be adapted to receive a metallic film such as silver, gold, or the like, or receive some other metallic coating which contains ions compatible with a conductive gel such as described below.

Attached to the lower surface 34 of conductive member 26, and in electrical continuity with conductive coating or film 36, is a conductive gel 38 attached to second end 30. The extent or area of conductive gel 38 coincides with the dimensions of the conductive member second end 30. For example, conductive gel 38 may occupy an area 3 cm square, and preferably an area 1.5 cm square, and most preferably in an area 1.5 cm by 1.3 cm. To be effective, the area of gel 38 can be larger, but if too small, the impedance becomes so high that the effectiveness tends to decrease. Moreover, with the smaller area comes a tendency for the gel to dry up quicker than if the conductive gel occupied a greater area. Conductive gel 38 may be made from any one of a number of conductive adhesives such as one disclosed in U.S. Pat. No. 5,012,810. Conductive gel 38 promotes enhanced electrical contact between the skin of the patient and the conductive coating or film 36 by acting as a continuous, conductive intermediary therebetween. Advantageously, the promotion of such a continuous conductive contact through the intermediary of the electrically conductive gel or adhesive material minimizes warm-up time and maintains the quality of the signal or trace. Moreover, the adhesive characteristic of gel 38 aids in avoiding motion artifacts, that is, disturbances in the trace due to relative movement between electrode 10 and the skin of the patient.

Figure 5:
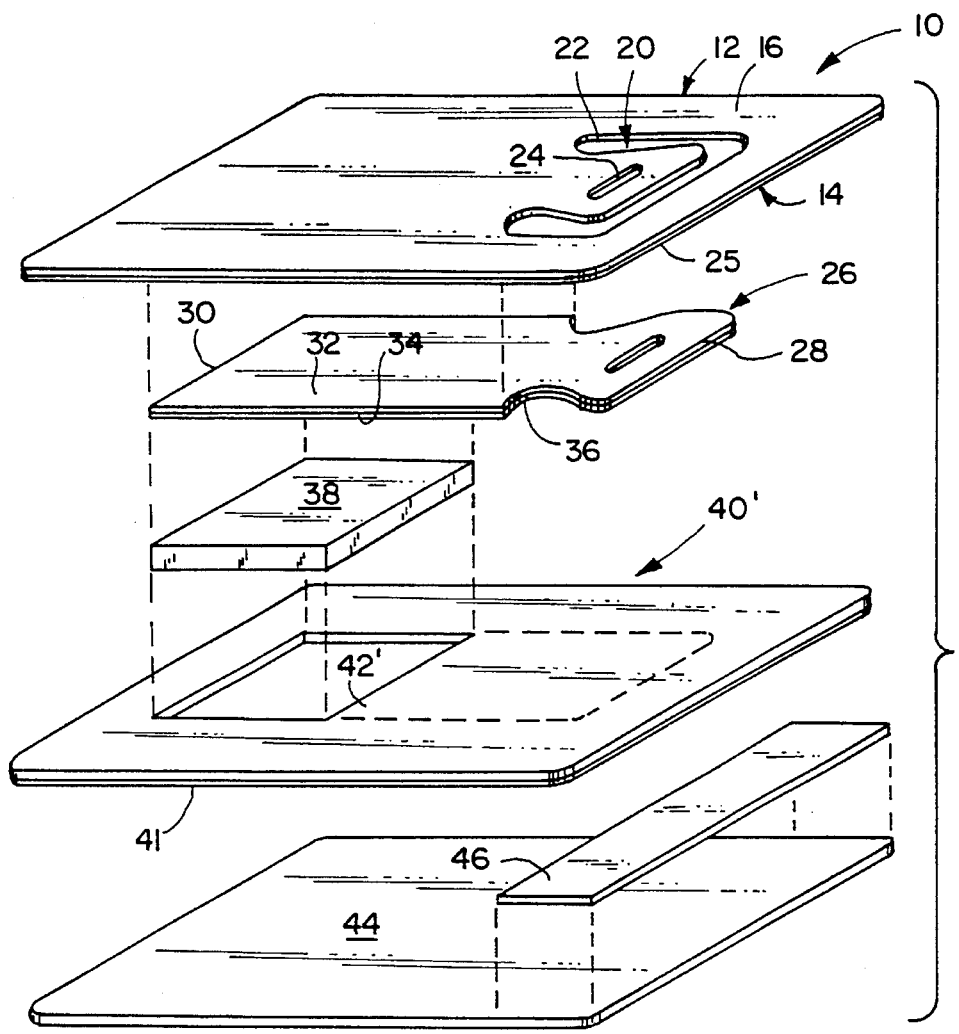
FIG. 5 is an exploded view of an alternate embodiment of the electrode of this invention.
Figure 6:
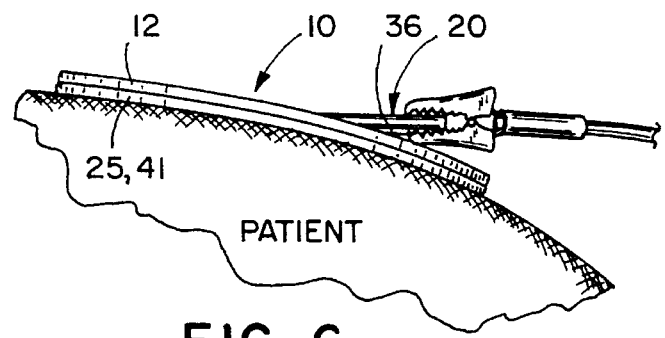
FIG. 6 is an elevation view of the electrode attached to a patient with the tab extending from the electrode.

Generally coplaner with conductive gel layer 38 is a lower insulative member or layer 40 which partially sandwiches conductive member 26 against top insulative layer 12 and retained there by adhesive layer 25. In one embodiment shown in FIG. 3, lower insulative layer 40 includes an edge portion 42 which extends from the edge of conductive gel layer 38 closest to the tab portion 20 to edge 39 of insulative layer 12. The remainder of insulative layer 40 is generally co-extensive with that portion of electrode 10 containing tab 20. In one embodiment, lower insulative layer 40 is made from a sheet of-MYLAR™ having a thickness ranging between 0.125 of a rail and 1 mil, and preferably ranging between 0.25 mil and 0.75 mil, and most preferably approximately 0.5 mil. In another embodiment shown in FIG. 5, lower insulative member 40' has an area co-extensive with that of the upper insulative layer 12 but includes a window portion 42' removed to allow conductive gel layer 38 to protrude therethrough. In the alternate embodiment, lower insulative layer 40' has the same thickness and is made from the same materials as in the preferred embodiment. In each of the embodiments, lower insulative layer 40, 40' is coated with a skin adhesive 41 similar to that described above on lower surface 14 of upper insulative layer 12.

The absence of an adhesive on lower surface 34 of conductive member 26 allows tab 20 and conductive member first end 28 to flex and extend from electrode 10 when the electrode is bent or attached to a curved surface. This freedom of tab 20 to extend from the electrode 10 permits easier connection of a clip or other electrode lead thereto, particularly when the electrode is attached to the patient. In an alternative, that half of insulative layer surface 14 overlying conductive member end 30 may be coated with a skin adhesive. Lower insulative layer 40 may be double-coated with adhesive to bind or adhere it to upper insulative layer 12 as well as to provide a skin adhesive to adhere the electrode to the patient. If this approach is adopted, it would be preferred to apply the adhesive to the upper surface of lower insulative layer 40 proximate peripheral edge 18 so that first end 28 of conductive member 26 is not adhered 16 lower insulative layer 40. The idea is to allow the stiffer conductive member 26 to extend tab 20 from electrode 10 when the electrode is flexed or attached to a curved portion of the patient.

The electrode assembly 10 described above is transported on a cover liner 44 preferably made from a 6 mil thick, silicone-coated polystyrene sheet, although other cover liners such as plastic, polycoated papers, and the like, may also be used. A portion of a release liner 46 underlies and is adhered to one end of lower insulative layer 40, and most preferably an end proximate peripheral edge 18, to allow the user to peel electrode 10 from the cover liner 44. The lower surface of release liner 46 does not bond or adhere to cover liner 44, thus providing a convenient parting surface to remove electrode 10 from cover liner 44.

Electrode 10 is manufactured using one or more webs of material which contribute the individual components to the electrode assembly line. For example, a continuous web of upper insulative material such as 12 progresses along an assembly line. If material 12 contains a skin adhesive along surface 14, it may be protected by a release which is removed prior to location of a conductive member 26 thereon. It is anticipated that conductive member 26 already contains the conductive coating thereon and oriented in the proper direction. The insulative web 12 and conductive member 26 may then receive the conducive gel 38 which is deposited on the lower surface 34 of conductive member 26 at the second end 30.

Prior to being combined with lower insulative layer 40, 40', the combined web 12, conductive member 26, and conductive gel 38 are passed through a die press which cuts U-shaped opening 22 and hole 24 to form tab 20 and the first end 28 of conductive member 26. Following formation of tab 20, lower insulative layer 40, 40' is adhered to upper insulative layer 12. This is followed by release liner 46 before passing through a second die which cuts the peripheral edge 18. The waste is removed and the completed electrodes are transferred to cover liner 46 for packaging. Other assembly or manufacturing routines may be used such as using the cover liner 44 as the web upon which the various elements are deposited, but in reverse to the step outlined above.

In operation, the physician, medical technician, or nurse peels each electrode from cover liner 44 by grasping electrode 10 at release liner 46. The electrode is placed at the appropriate location on the patient and pressed into place so that conductive gel 38 makes contact with the skin. If electrode 10 is placed on a portion of the patient which is curved, tab 20 will extend slightly away from lower insulative layer 40, 40' and have a relief greater than the remainder of upper insulative layer 12. With the tab 20 so exposed, the operator may then readily attach an electrode lead such as a well-known alligator clip or sliding clasp lead manufactured by Tronomed, Inc., of San Juan Capistrano, Calif. Such electrode leads contact the lower surface 34 of conductor member 26 and the conductive coating 36, placing conductive gel 38 in electrical continuity with the diagnostic equipment attached by the leads. Some slide clasp electrodes include a projection which extends into tab aperture 24, allowing the electrode lead to swivel slightly relative to the electrode without excessively disturbing the electrode or breaking the electrical contact with tab 20.

FIGS. 7 and 8 show an alternative embodiment of the invention in which a conductive connector is secured to tab 20 of the electrode. The conductive connector comprises a post 60, including a circular base 61, a shank 62 projecting from base 61 and a head 63 which is slightly larger than shank 62 in order to accommodate a snap-fit lead. Preferably, post 60 is made of a carbon or graphite-containing polymeric material.

In this embodiment, aperture 24' in tab 20 is circular, rather than an elongated slot. Shank 62 of post 60 projects upwardly through the aperture 24' in both conductive member 26 and the upper insulative layer 12. Conductive base 61 engages conductive member 26. Base 61 is held tightly against conductive layer 26 by means of a semi-flexible washer 70 which is force-fit over head 63 and shank 62 of post 60. The inner diameter of washer 70, which is preferably made of a polymeric material, is narrower than the diameter of the shank 62 of post 60. By forcing washer 70 tightly down towards base 61, a very tight compression fit is achieved between post and washer assembly 60-70 and conductive member 26 and insulative layer 12 of the electrode.

Figure 10:
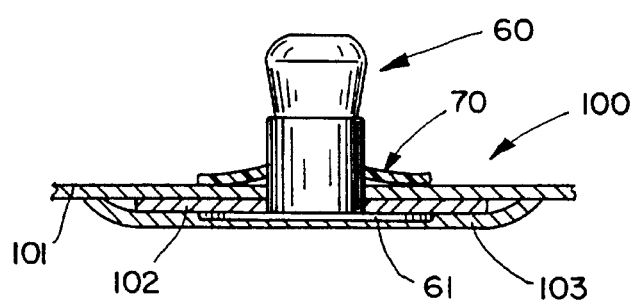
FIG. 10 is a cross section taken through X—X of FIG. 9.

FIGS. 9 and 10 disclose an alternative embodiment electrode 100 utilizing the conductive polymeric post 60 and washer 70. In this electrode, a nonconductive web 101 which is adhesively coated on its underside overlies and extends beyond the perimeter of an underlying conductive layer 102. Web 101 and conductive layer 102 are sandwiched between the circular base 61 of post 60 and washer 70. Unlike the tab electrode 10 previously described, the conductive gel layer 103 of alternative embodiment electrode 100 lies directly under circular base 61 of post 60, and also extends beneath the entirety of conductive layer 102. The adhesive undersurface of web 101 extends beyond the perimeter of gel layer 103 and thereby aids in adhering electrode 100 to the patient's skin.

It will be noted that conductive connector 60 is preferably not plated with a metal surface. Thus, conductivity is achieved solely by reason of the carbon or graphite content of the polymeric material of which post 60 is made.

In view of the above description, those of ordinary skill in the art may envision various modifications which would not depart from the inventive concepts disclosed herein. It is expressly intended, therefore, that the above description should be considered as only that of the preferred embodiment. The true spirit and scope of the present invention may be determined by reference to the appended claims.

The embodiments of the invention in which an exclusive property or privilege is claimed are defined as follows:

1. A tab electrode, comprising:

a flexible insulative layer having first and second opposite sides terminating in a peripheral edge and having a tab inboard of said peripheral edge such that a portion of said flexible insulative layer encompasses said tab;

a conductive member, having a first end and a second end, adhered to said first side of said insulative layer with said second end underlying said tab, said conductive member having a stiffness greater than said flexible insulative layer;

a conductive gel attached to said first end of said conductive member on a side opposite from said flexible insulative layer; and a lower insulative member adhered to said first side of said flexible insulative layer and underlying at least said tab and a portion of said flexible insulative layer encompassing said tab, and leaving exposed at least a portion of said conductive gel.

2. The tab electrode as defined in claim 1, including:
   an adhesive on said first side of said flexible insulative layer; and
   an adhesive on a side of said lower insulative member opposite that adhered to said first side of said flexible insulative layer.

3. The tab electrode as defined in claim 2, including a conductive coating deposited on said conductive member on a side opposite that adhered to said first side of said flexible insulative layer.

4. The tab electrode as defined in claim 3, wherein said conductive coating is a metallic film compatible with said conductive gel.

5. The tab electrode as defined in claim 4, wherein said metallic film is silver/silver chloride.

6. The tab electrode as defined in claim 2, wherein said second end of said conductive member is adhered to said first side of said flexible insulative layer.

7. The tab electrode as defined in claim 6, wherein said tab and said second end of said conductive member extend from the electrode when the electrode is flexed.

8. The tab electrode as defined in claim 1, wherein said flexible insulative layer is made from a non-woven material.

9. The tab electrode as defined in claim 8, wherein said non-woven material is a spun-bond material.

10. The tab electrode as defined in claim 8, wherein said non-woven material is a polymeric material.

11. The tab electrode as defined in claim 1, wherein said lower insulative layer includes a window for receiving said conductive gel therethrough.

12. The tab electrode as defined in claim 1, wherein said lower insulative layer has an upper and lower surface coated with an adhesive.

13. The electrode of claim 1 in which a conductive connector is positioned on said tab in electrical contact with said conductive member, said connector facilitating connection of a lead wire to said electrode.

14. The electrode of claim 13 in which said connector comprises a snap post to which said lead wire can be snap connected.

15. The electrode of claim 14 in which said snap post is formed of a carbon-containing polymer material.

16. The electrode of claim 15 in which said snap post comprises a base and a shank projecting from said base, said base having a larger lateral cross-sectional diameter than said shank; said tab and said second end of said conductive member including an aperture therein; said shank of said snap post projecting through said aperture and said base engaging said second end of said conductive member; said connector base being held tightly against said conductive member by a semiflexible washer having an inside diameter smaller than the lateral cross-sectional diameter of said shank, said washer being press-fit over said snap post and pushed snugly down said shank against said tab, to thereby sandwich said tab and said conductive member tightly between said washer and said base.

17. The electrode of claim 16 in which said washer is made of a polymeric material.

18. The electrode of claim 14 in which said snap post comprises a base and a shank projecting from said base, said base having a larger lateral cross-sectional diameter than said shank; said tab and said second end of said conductive member including an aperture therein; said shank of said snap post projecting through said aperture and said base engaging said second end tab portion of said conductive member; said connector base being held tightly against said conductor by a semiflexible washer having an inside diameter smaller than the lateral cross-sectional diameter of said shank, said washer being press-fit over said snap post and pushed snugly down said shank against said tab, to thereby sandwich said tab and said conductive member tightly between said washer and said base.

19. A tab electrode, comprising:
   a flexible upper insulative layer having a first and second sides terminating in a peripheral edge;
   a flexible conductor adhered to said first side of said flexible insulative layer and having an area less than said insulative layer first side, said conductor having a first portion and a second portion and a stiffness greater than said flexible upper insulative layer;
   a tab defined in said upper insulative layer and overlying said second portion of said conductor, said tab inset from said peripheral edge of said upper insulative layer;
   a conductive gel attached to said first portion of said conductor on a side opposite said first side of said insulative layer; and
   a lower insulative layer adhered to said first side of said upper insulative layer and exposing said conductive gel.

20. The tab electrode as defined in claim 19, wherein said conductor includes conductive material selected from the group consisting of conductive foils, conductive films, and conductive coatings.

21. The tab electrode as defined in claim 20, wherein said conductor includes a polymeric substrate for receiving said conductive material.

22. The tab electrode as defined in claim 20 wherein said conductive material is printed on said conductor.

23. The tab electrode as defined in claim 19, wherein said lower insulative member has a shape coextensive with said upper insulative layer and has a window defined therein for said conductive gel.

24. The tab electrode as defined in claim 19, wherein said lower insulative member underlies said tab defined in said upper insulative layer.

25. The electrode of claim 19 in which a conductive connector is positioned on said tab, in electrical contact with said conductor, said connector facilitating connection of a lead wire to said electrode.

26. The electrode of claim 25 in which said connector comprises a snap post to which said lead wire can be snap connected.

27. The electrode of claim 26 in which said snap post is formed of a carbon-containing polymer material.

28. The electrode of claim 27 in which said snap post comprises a base and a shank projecting from said base, said base having a larger lateral cross-sectional diameter than said shank; said tab said second portion of said conductor including an aperture therein; said shank of said snap post projecting through said aperture and said base engaging said conductor; said connector base being held tightly against said conductor by a semi-flexible washer having an inside diameter smaller than the lateral cross-sectional diameter of said shank, said washer being press-fit over said snap post and pushed snugly down said shank against said tab to thereby sandwich said tab conductor tightly between said washer and said base.

29. The electrode of claim 28 in which said washer is made of a polymeric material.

30. The electrode of claim 26 in which said snap post comprises a base and a shank projecting from said base, said base having a larger lateral cross-sectional diameter than said shank; said tab said second portion of said conductor including an aperture therein; said shank of said snap post projecting through said aperture and said base engaging said tab portion of said conductor; said connector base being held tightly against said conductor by a semi-flexible washer having an inside diameter smaller than the lateral cross-sectional diameter of said shank, said washer being press-fit over said snap post and pushed snugly down said shank against said tab, to thereby sandwich said tab and conductor tightly between said washer and said base.

31. An electrode, comprising:

an upper insulative layer having first and second sides terminating in a border;

a tab defined by a cut-out in said upper insulative layer inside said border; and a conductor adhered to said first side of said upper insulative layer, and having a tab portion underlying said tab defined by said upper insulative layer and a pad portion spaced therefrom, said tab portion having a stiffness greater than said upper insulative layer such that said tab and conductor protrude from the electrode when said first side of said upper insulative layer is concave.

32. The electrode of claim 31 in which a conductive connector is positioned on said tab, in electrical contact with said conductor, said connector facilitating connection of a lead wire to said electrode.

33. The electrode of claim 32 in which said connector comprises a snap post to which said lead wire can be snap connected.

34. The electrode of claim 33 in which said snap post is formed of a carbon-containing polymer material.

35. The electrode of claim 34 in which said snap post comprises a base and a shank projecting from said base, said base having a larger lateral cross-sectional diameter than said shank; said tab portion including an aperture therein; said shank of said snap post projecting through said aperture and said base engaging said conductor; said connector base being held tightly against said conductor by a semi-flexible washer having an inside diameter smaller than the lateral cross-sectional diameter of said shank, said washer being press-fit over said snap post and pushed snugly down said shank against said tab, to thereby sandwich said tab and said conductor tightly between said washer and said base.

36. The electrode of claim 35 in which said washer is made of a polymeric material.

37. The electrode of claim 33 in which said snap post comprises a base and a shank projecting from said base, said base having a larger lateral cross-sectional diameter than said shank; said tab and tab portion including an aperture therein; said shank of said snap post projecting through said aperture and said base engaging said conductor; said connector base being held tightly against said conductor by a semi-flexible washer having an inside diameter smaller than the lateral cross-sectional diameter of said shank, said washer being press-fit over said snap post and pushed snugly down said shank against said tab to thereby sandwich said tab and said conductor tightly between said washer and said base.

\* \* \* \* \*

UNITED STATES PATENT AND TRADEMARK OFFICE
CERTIFICATE OF CORRECTION

PATENT NO. : 5,566,672
DATED : October 22, 1996
INVENTOR(S) : Faasse, Jr.

It is certified that error appears in the above-identified patent and that said Letters Patent is hereby corrected as shown below:

Col. 2, line 43, "file" should be --the--;

Col. 3, line 2, delete "and";

Col. 4, line 47, "rail" should be --mil--;

Col. 5, line 7, "16" should be --to--;

Col. 8, line 3, "conductor" second occurrence should be --conductive member--;

Col. 8, line 62, after "tab" insert --and--; and

Col. 10, line 6, "said tab portion" should be --said tab and tab portion--.

Signed and Sealed this

Twenty-second Day of July, 1997

Attest:

BRUCE LEHMAN

Attesting Officer

Commissioner of Patents and Trademarks